(12) United States Patent
Elliott (10) Patent No.: US 11,020,044 B2
(45) Date of Patent: Jun. 1, 2021

(54) MULTIPLE WELL EPICUTANEOUS TEST PATCH ARRAY

(71) Applicant: John Elliott, Edmonton (CA)

(72) Inventor: John Elliott, Edmonton (CA)

(73) Assignee: Immunoderm Inc., Edmonton (CA)

( * ) Notice: Subject to any disclaimer, the term of this patent is extended or adjusted under 35 U.S.C. 154(b) by 312 days.

(21) Appl. No.: 16/162,236

(22) Filed: Oct. 16, 2018

(65) Prior Publication Data

US 2019/0110737 A1    Apr. 18, 2019

Related U.S. Application Data

(60) Provisional application No. 62/573,269, filed on Oct. 17, 2017.

(51) Int. Cl.
*A61B 5/00* (2006.01)
*A61F 13/02* (2006.01)
*A61F 13/00* (2006.01)

(52) U.S. Cl.
CPC .............. *A61B 5/411* (2013.01); *A61B 5/441* (2013.01); *A61B 5/6823* (2013.01); *A61B 5/6833* (2013.01); *A61F 13/02* (2013.01); *A61F 13/023* (2013.01); *A61F 13/0226* (2013.01); *A61F 2013/00434* (2013.01); *A61F 2013/00829* (2013.01)

(58) Field of Classification Search
CPC ...... A61F 13/00; A61F 13/02; A61F 13/0226; A61F 13/023; A61F 13/0253; A61F 13/2059; A61F 2013/00361; A61F 2013/00434; A61F 2013/00829; A61F 2013/00655; A61F 2013/00578; A61F 2013/00612; A61F 2013/00634; B32B 3/06; B32B 3/12; B32B 3/14; B32B 3/16; B32B 3/20; B32B 3/26; B32B 3/263; B32B 3/30
See application file for complete search history.

(56) References Cited

U.S. PATENT DOCUMENTS 4,450,844 A    5/1984    Quisno
4,836,217 A    6/1989    Fischer
(Continued)

FOREIGN PATENT DOCUMENTS

EP    0540577        8/2001
EP    0540577 B2 *  8/2001    ......... A61B 10/0035
(Continued)

OTHER PUBLICATIONS

Hamann et al., A Contemporary Fischer-Maibach Investigation: Variations in Patch Test Delivery Systems and Implications for Standardization, Nov. 2013, American Contact Dermatitis Society, vol. 24, p. 303 (Year: 2013).*
(Continued)

*Primary Examiner* — Catherine B Kuhlman
*Assistant Examiner* — Severo Antonio P Lopez
(74) *Attorney, Agent, or Firm* — Craig Sherburne (57) ABSTRACT

Described is a novel epicutaneous test plaster useful for the application of test substances for direct and continuous contact with the skin of a human patient. The plaster comprises a support lattice with a flexible carrier lattice adhered thereto, the combination forming a series of test chambers capable of receiving test substances for application to the skin.

12 Claims, 11 Drawing Sheets

(56) References Cited

U.S. PATENT DOCUMENTS

| | | | |
|---|---|---|---|
| 5,182,081 A | 1/1993 | Hedegaard | |
| 5,614,167 A | 3/1997 | Hansen | |
| 6,142,954 A | 11/2000 | Anhauser | |
| 7,798,976 B2 | 9/2010 | Nlklasson | |
| 2011/0264003 A1 | 10/2011 | Hamann | |

FOREIGN PATENT DOCUMENTS

| | | | | |
|---|---|---|---|---|
| EP | 3108862 A1 | * | 12/2016 | ........... A61F 7/0097 |
| NL | 8701577 A1 | * | 2/1989 | ............. A61B 10/00 |
| WO | WO-03059171 A1 | * | 7/2003 | ......... A61B 10/0035 |
| WO | WO-2011144888 A1 | * | 11/2011 | ........... A61F 13/023 |
| WO | WO-2017032400 A1 | * | 3/2017 | ........... A61B 5/6886 |

OTHER PUBLICATIONS

Hamann, Dathann, "A Contemporary Fischer-Maibach Investigation:Variations in Patch Test Delivery Systems and Implications for Standardization" Dermatitis,vol. 24, No. 6, Nov./Dec. 2013, pp. 302-312.
T.R.U.E. Test® (Allergen Patch Test) Reference Manual, 2018 Smart Practice.

\* cited by examiner

Figure 11

MULTIPLE WELL EPICUTANEOUS TEST PATCH ARRAY

CROSS-REFERENCE TO RELATED APPLICATIONS

The present application claims priority from U.S. Provisional Patent Application No. 62/573,269 filed Oct. 17, 2017, such application is expressly incorporated by reference herein for all purposes.

FIELD OF THE INVENTION

The present invention pertains to an application aid useful for assessment of assessment of dermatological sensitivities or allergic responses to compounds through use of an epicutaneous test patch array.

BACKGROUND OF THE INVENTION

All of the publications, patents and patent applications cited within this application are herein incorporated by reference in their entirety to the same extent as if the disclosure of each individual publication, patent application or patent was specifically and individually indicated to be incorporated by reference in its entirety.

Epicutaneous plasters (also referred to as patches) are commonly used for testing of patients for allergies or sensitivities to compounds, such as known allergens or haptens; in which a series of suspected haptens are loaded onto the epicutaneous plaster, which is then attached to the skin of a patient((s)) for up to 7 days, following which the plaster is removed and the skin of the patient observed for irritation, inflammation or other reactions associated with allergies or sensitivities. As well as needing to maintain separation between haptens being tested on a patient, the epicutaneous patch must also allow flexibility so as to maintain contact between the loaded hapten and the patient's skin. Further, it has become more common in clinical practice to test greater than 20 haptens concurrently; and therefore it can be an inconvenience to the clinical practitioner to use epicutaneous plasters that are limited to less than 12 chambers capable of receiving haptens.

The art describes test plasters, or test patches, useful for providing continuous contact of a test substance to selected areas of skin of a patient. For example, WO1998025521 describes an absorptive material placed between the skin of the patient and a resilient carrier film made of a polymer material. By way of another example, U.S. Pat. No. 7,798,976 describes a epicutaneous test plaster with a plurality of test chambers, each test chamber comprised of a support element secured to a carrier, a carrier, a frame shaped foam plastic lattice and a second lattice of adhesive interposed between the foam plastic and support element.

Although useful for maintaining contact between a test substance (for example a hapten) and the skin, the prior art devices suffer from limitations; for example, in identifying or correlating chambers with the hapten loaded into the chamber once applied to the skin. By way of another example, prior art devices were difficult to handle once the support element was removed, such as during loading. By way of another example, the epicutaneous plasters, due to their design, have limitations to their size and/or number of separated chambers they may contain. This is a function of the volume of hapten generally used in clinical practise, the orientation and ordering of the chambers within the epicutaneous plaster, and the use of wells or metal or stiff plastic which limits the ability to maintain adhesion of the chamber to the skin during movement of the patient.

The art is in need of a epicutaneous plaster that allows improved loading of haptens into the plaster, improved handling during and following loading of the haptens, and allows for the implementation of larger number of test chambers on a contiguous plaster.

SUMMARY OF THE INVENTION

An object of the present invention is to provide for an epicutaneous test plaster which provides for improved loading of haptens, improved flexibility on a patient, and the ability to include more test chambers within a single epicutaneous test plaster.

The present invention provides for an epicutaneous test plaster comprising a support lattice of absorbent paper adhered with a moisture barrier layer containing a first multiplicity of holes; a flexible carrier lattice containing a second multiplicity of holes, said flexible carrier lattice including an adhesive layer for removable adhesion of the epicutaneous plaster to a skin portion; a removable cover layer extending over all the adhesive layer of said flexible carrier lattice, and a plurality of test chambers distributed over the support lattice of absorbent paper adhered with a moisture barrier layer; wherein the second multiplicity of holes on the flexible carrier lattice is greater than the first multiplicity of holes on the support lattice of absorbent paper adhered with a moisture barrier; wherein said flexible carrier lattice is adhered to the support lattice on the side opposite to the moisture barrier layer; wherein the plurality of test chambers are formed by way of second multiplicity of holes in the flexible carrier lattice describing a frame around a contiguous portion of the support lattice; wherein a subset of the first multiplicity of holes on the support lattice align with the second multiplicity of holes in the flexible carrier lattice; and wherein the removable cover layer is removably secured by way of the adhesive layer of the flexible carrier lattice.

In one embodiment of the present invention, the flexible carrier lattice is comprised of polyethylene foam and the adhesive layer is comprised of a medical grade adhesive such as acrylics, cyanoacrylates, silicones or polyurethanes. In a preferred embodiment the polyethylene foam has a thickness of between 0.4 mm and 0.6 mm, and in a still more preferred embodiment the polyethylene foam is 0.5 mm in thickness. In a further embodiment the removable cover layer is a lattice with a third multiplicity of holes. In an even further embodiment the third multiplicity of holes align with the second multiplicity of holes in the flexible carrier lattice.

In yet another embodiment, the present invention comprises a support lattice comprising a moisture barrier layer containing a first multiplicity of holes; a flexible carrier lattice containing a second multiplicity of holes, said flexible carrier lattice including an adhesive layer for removable adhesion of the epicutaneous plaster to a skin portion; a removable cover layer extending over all the adhesive layer of said flexible carrier lattice, and a plurality of test chambers distributed over the support lattice of a moisture barrier layer; wherein the second multiplicity of holes on the flexible carrier lattice is greater than the first multiplicity of holes on the support lattice of a moisture barrier; wherein said flexible carrier lattice is adhered to the support lattice; wherein the plurality of test chambers are formed by way of second multiplicity of holes in the flexible carrier lattice describing a frame around a contiguous portion of the support lattice; wherein a subset of the first multiplicity of holes on the support lattice align with the second multiplicity of holes in the flexible carrier lattice; and wherein the removable cover layer is removably secured by way of the adhesive layer of the flexible carrier lattice.

In another embodiment at least one unique chamber identifier is printed on the moisture barrier layer proximate to a test chamber.

DETAILED DESCRIPTION OF THE PRESENT INVENTION

According the present invention, the individual test chambers are formed by the joining of two lattices, a support lattice and a flexible carrier lattice, where the number of holes in the flexible carrier lattice are greater than the number of holes in the support lattice. The layering of the support lattice overtop the flexible carrier lattice results in the formation of wells formed with a base of the support lattice, and holes passing through both the support lattice and the flexible carrier lattice.

Figure 1:
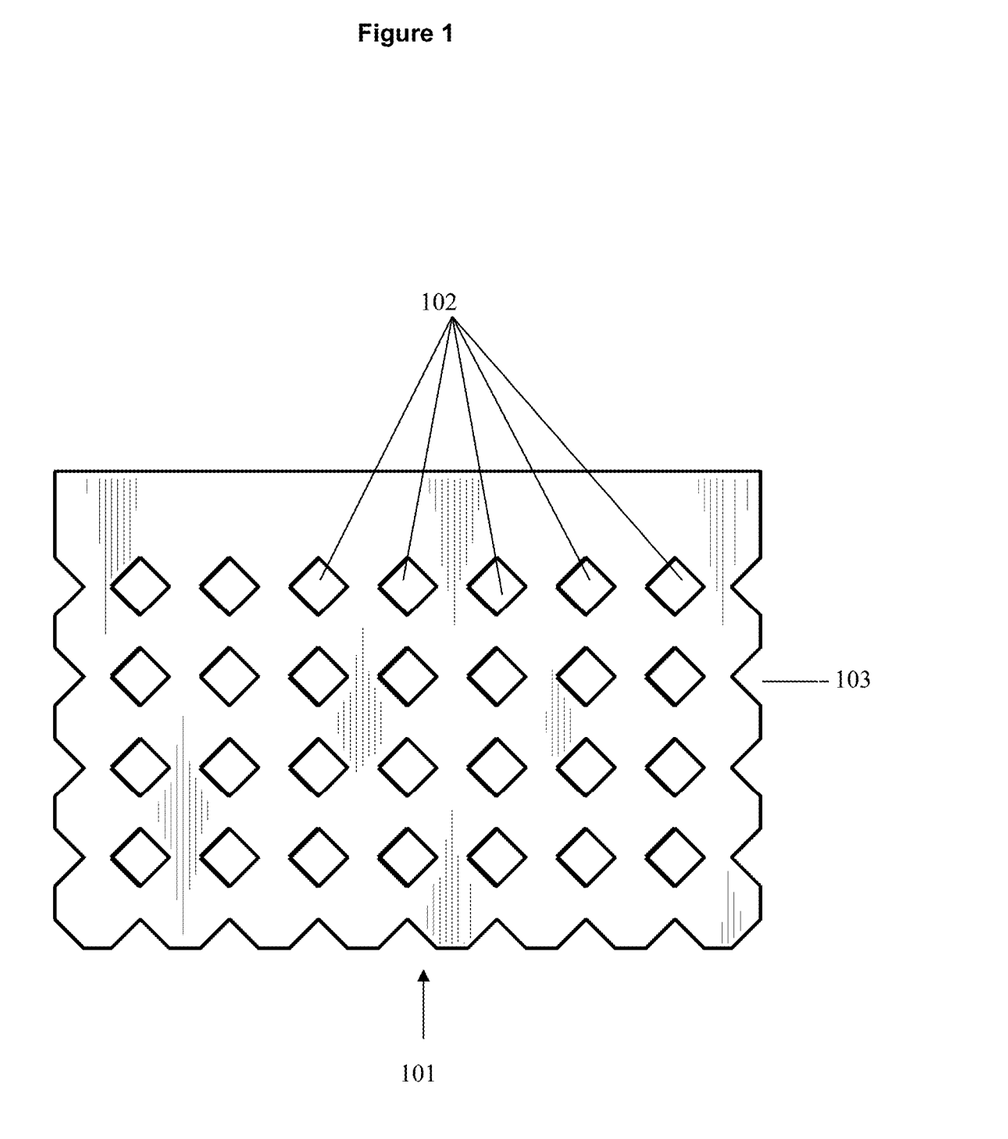
FIG. 1 shows a support lattice of a preferred embodiment of the present invention.
Figure 9:
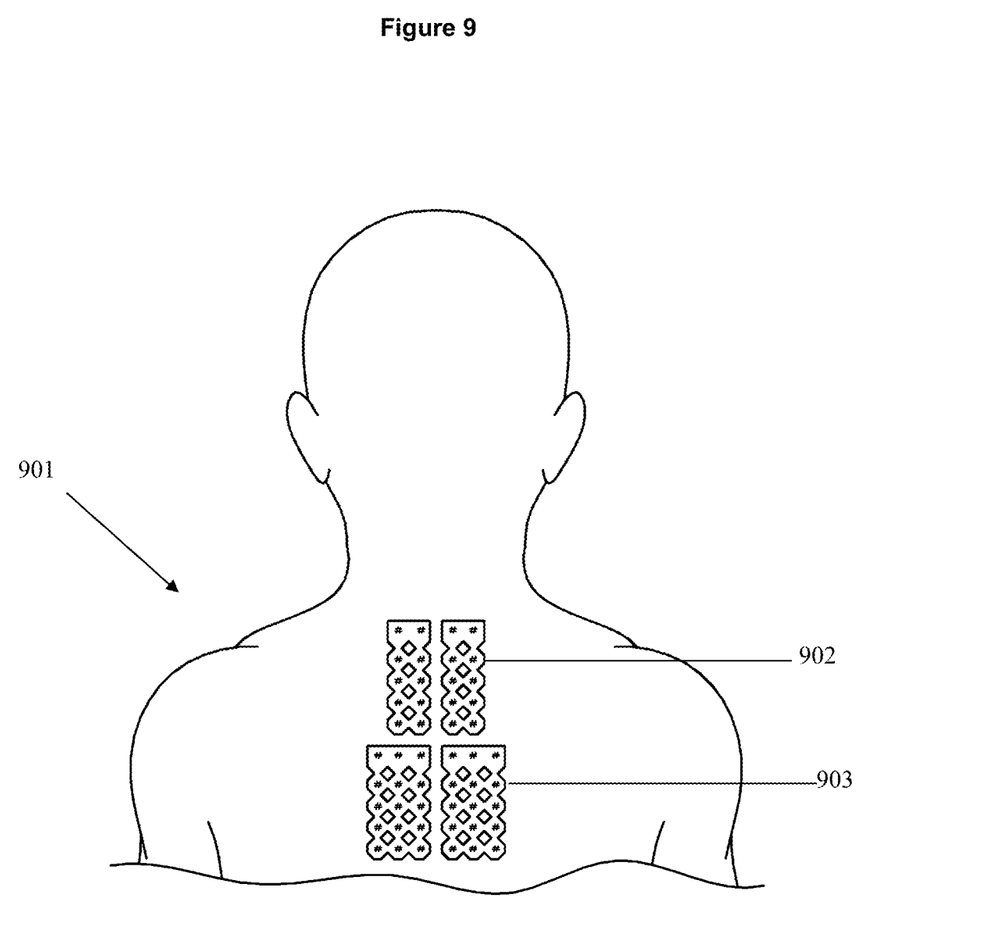
FIG. 9 Shows one embodiment of the present invention placed on a human subject, with the test plaster segmented for easy placement on the subject.
Figure 10:
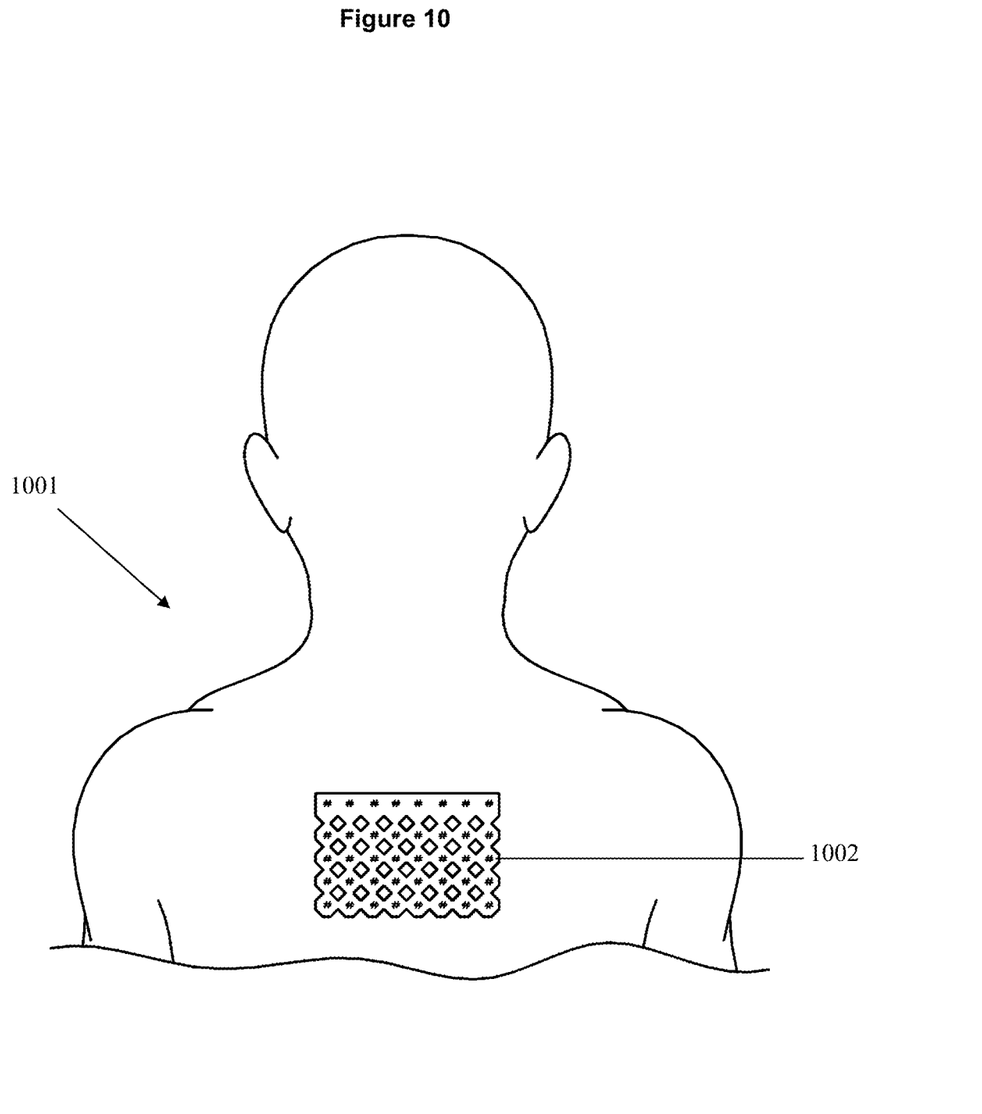
FIG. 10 Shows another embodiment of the present invention placed on a human subject, with the test plaster placed integral on the subject.

FIG. 1 shows the support lattice, 101, with a series of holes, 102, passing through the support lattice 101. Optional indentations 103 are shown, the indentations arising from one possible manufacturing process, where a multiplicity of epicutaneous test plasters may be manufactured from larger sheets of support lattice, the individual epicutaneous test plasters may be produced through cutting of the larger sheet into individual epicutaneous test plasters. Holes 102, and optional indentations 103, serve to provide increased flexibility of the epicutaneous test plaster, of particular relevance when placed upon a patient, as shown in FIG. 9 and FIG. 10.

Figure 2:
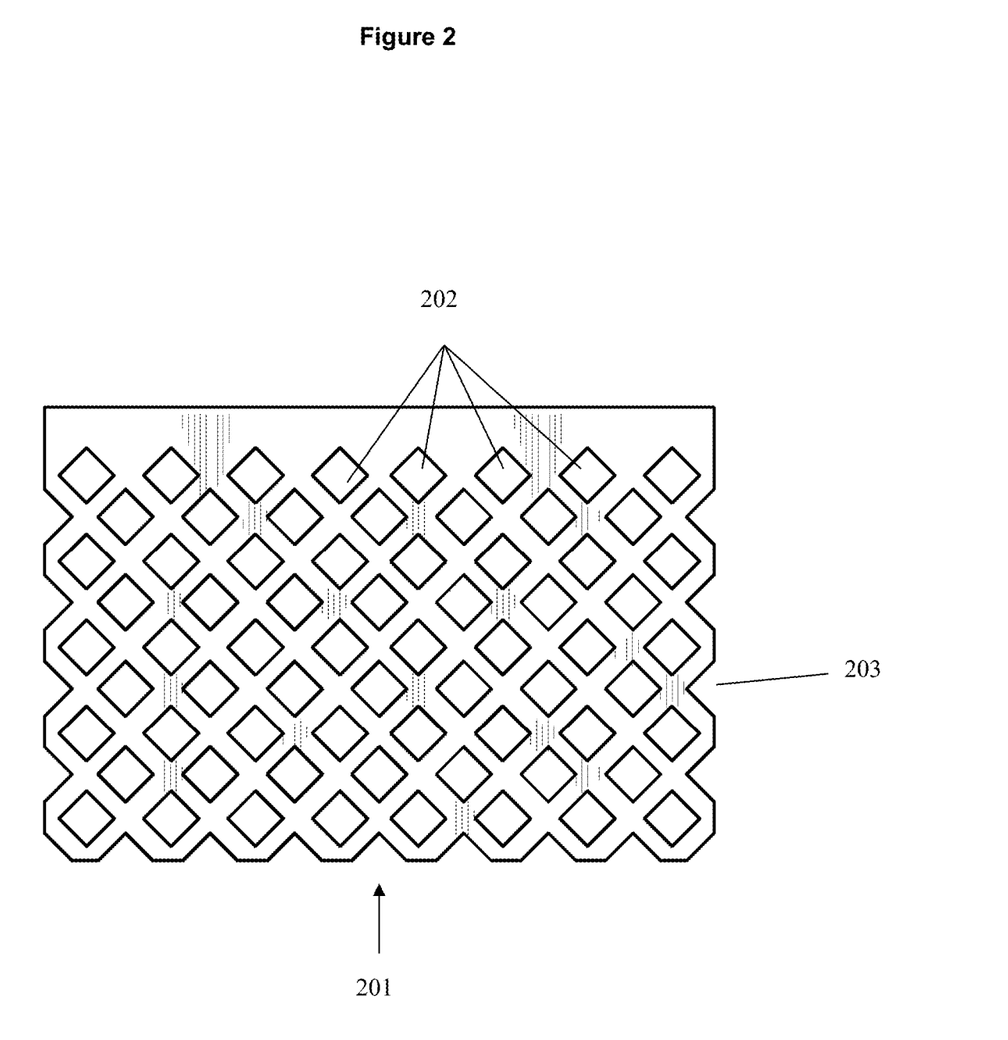
FIG. 2 shows the flexible carrier lattice of a preferred embodiment of the present invention.

FIG. 2 shows the flexible carrier lattice, 201, with a series of holes, 202, passing through flexible carrier lattice 201. Optional indentations 203 are shown, the indentations arising from one possible manufacturing process, where a multiplicity of epicutaneous test plasters may be manufactured from larger sheets of support lattice, the individual epicutaneous test plasters may be produced through cutting of the larger sheet into individual epicutaneous test plasters.

Figure 3:
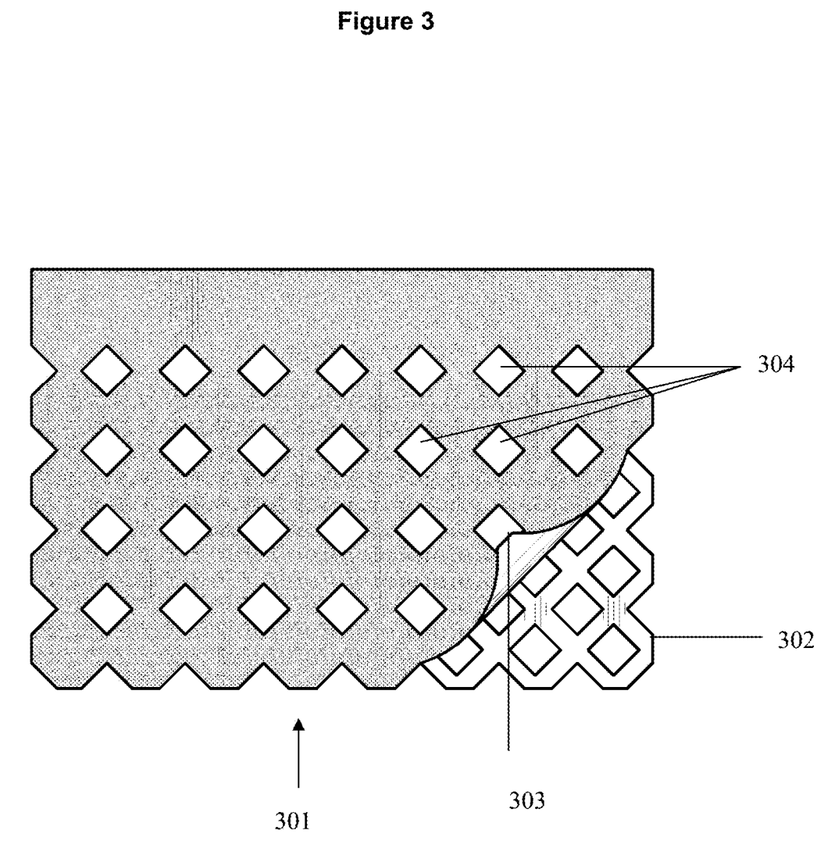
FIG. 3 shows a one embodiment of the present invention, demonstrating the interaction between the support lattice and the flexible carrier lattice, with the support lattice being peeled from the flexible carrier lattice.

FIG. 3 shows the underside of the epicutaneous test plaster of the present invention, being the side exposed upon placement on the skin of a patient. Epicutaneous test plaster, 301, formed by the placement of support lattice 303 over flexible carrier lattice 302. The alignment of the holes between support lattice 303 and flexible carrier lattice 302 results in holes 304 passing through the epicutaneous test plaster 301, representing the alignment of holes in support lattice 303, with a subset of holes in flexible carrier lattice 302. Holes 304 provide improved flexibility to the epicutaneous test plaster, of particular utility when placed in contact with a patient's skin, maintaining contact of the hapten with the skin and reducing or eliminating leaking of the hapten from the test chambers.

Figure 4:
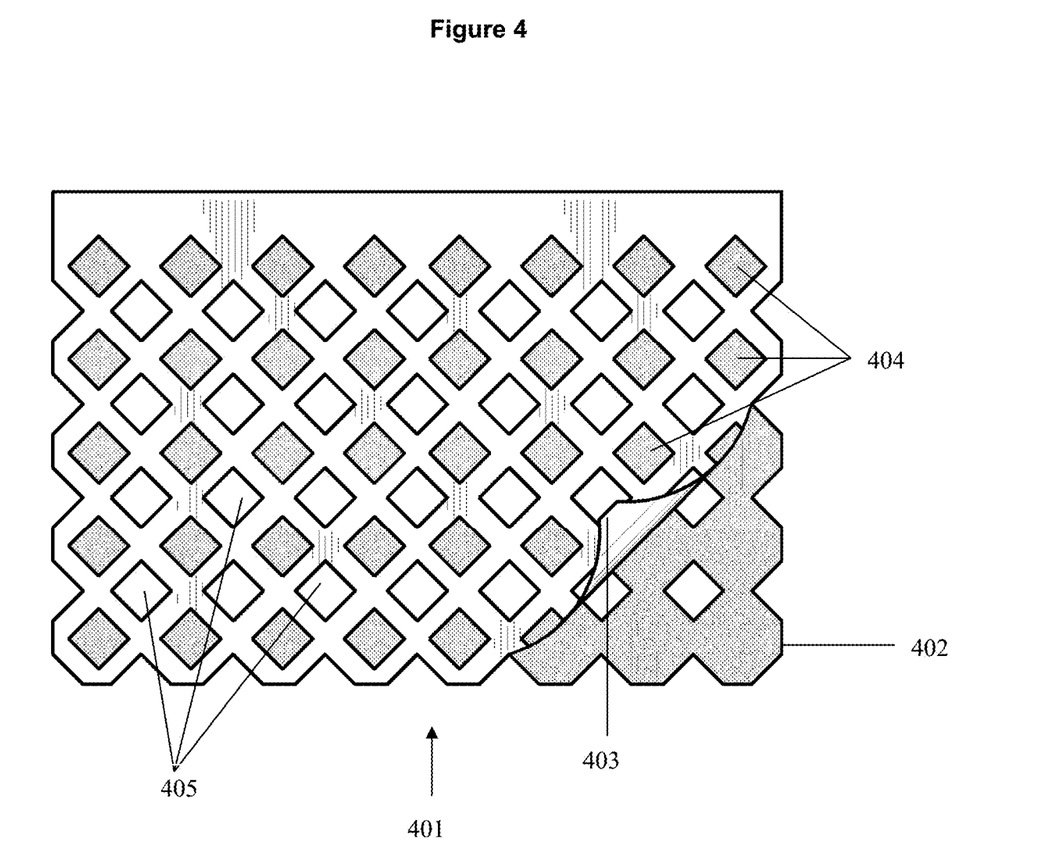
FIG. 4 shows a one embodiment of the present invention, demonstrating the interaction between the support lattice and the flexible carrier lattice, with the flexible carrier lattice being peeled from the support lattice.

FIG. 4 shows an illustration of the chambers formed by the application of the support lattice 402 onto the flexible carrier lattice 403, forming a preferred embodiment of the present invention, epicutaneous test plaster 401. Shaded areas 404 represent the chambers of the epicutaneous test plaster, with the floor of the chamber formed by the support lattice 402, and unshaded areas 405 representing the holes formed by alignment of a subset of holes in support lattice 402 and flexible carrier lattice 403.

The support lattice 402 is contemplated to be comprised of a bottom layer that is impermeable to fluid forming a barrier to transfer of moisture, and a layer of absorbent material for trapping and containing a hapten. The present invention is not contemplated to be limited to one form of support lattice, though capability to maintain the hapten within the chamber, prevent loss of the hapten perpendicular to the plane of the support lattice, for example by evaporation; and limit transfer of the hapten on the plane of the support lattice which would result in the appearance of "leakage" of the hapten between chambers, or reduction of the surface concentration of hapten in contact with a patient's skin. In a preferred embodiment of the present invention, the support lattice is formed by a paper lined with polyethylene plastic. One example product that may be used as a support lattice is known as "Whatman Benchkote", of total thickness of 0.4 mm to 0.5 mm.

Figure 5:
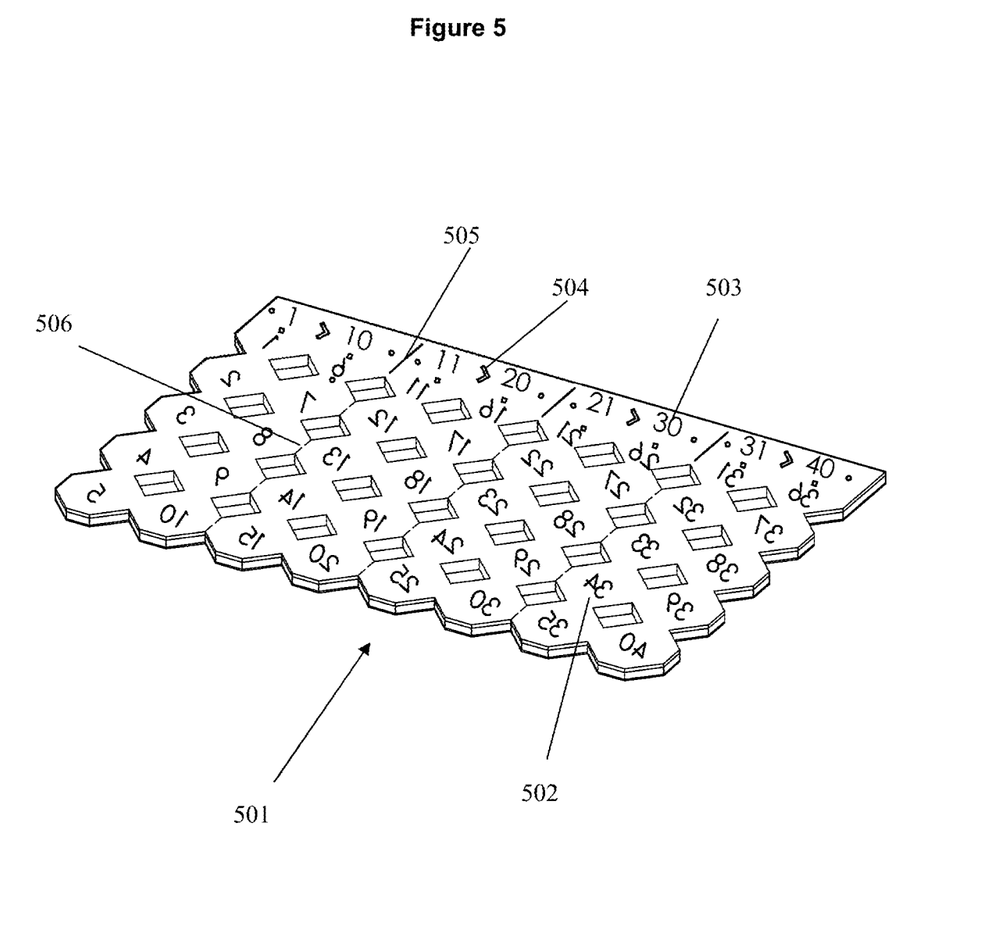
FIG. 5 Shows the underside of a preferred embodiment of the present invention, with exemplary markings on the support lattice.

It is also contemplated that the support lattice 402 be optionally comprised only of a moisture barrier layer, for example a layer of polyethylene plastic, with no layer of absorbent material forming part of the support lattice. This is particularly useful for haptens contained in a petroleum jelly or other viscous medium, and allows for improved visibility of optional markings 502. This also eliminates risk of leakage of the haptens between test chambers, the leakage occurring through the absorbent materials; such as can happen with haptens in a non-viscous medium such as water or alcohol. In such a case it is contemplated to use a moisture barrier layer for the support lattice, without absorbent material, and utilizing a small piece of absorbent material placed within the chamber (for example, filter paper) to absorb the liquid medium carrying the hapten prior to application of the epicutaneous test plaster to the patient, as contemplated herein.

As used in clinical practice, an epicutaneous test plaster is placed on the skin of a patient, with the chambers containing a hapten placed with the open side of the chamber placed against the skin, and the bottom layer that is impermeable to fluid, forming part of the bottom of the chamber, opposing the open side of the chamber, exposed to the environment. Labelling of this bottom layer is contemplated as part of the present invention, one example of this labeling presented in FIG. 5. Within the epicutaneous test plaster 501 are labeled undersides of chambers, 502, in a preferred embodiment the labelling is with reversed text. The reversal of the text, exemplified by 502, assists in the filling of the chambers, wherein the epicutaneous test plaster is usually oriented such that the bottom layer of the support lattice, which is impermeable to fluid, is placed on a flat surface, usually a lightbox. As such, the reversed labelling 502 is viewed, with the viewer looking through the chamber opening, as being in the original "sense" orientation. This assists in the placement of haptens within the chamber, and proper documentation of the particular haptens in each chamber.

Figure 6:
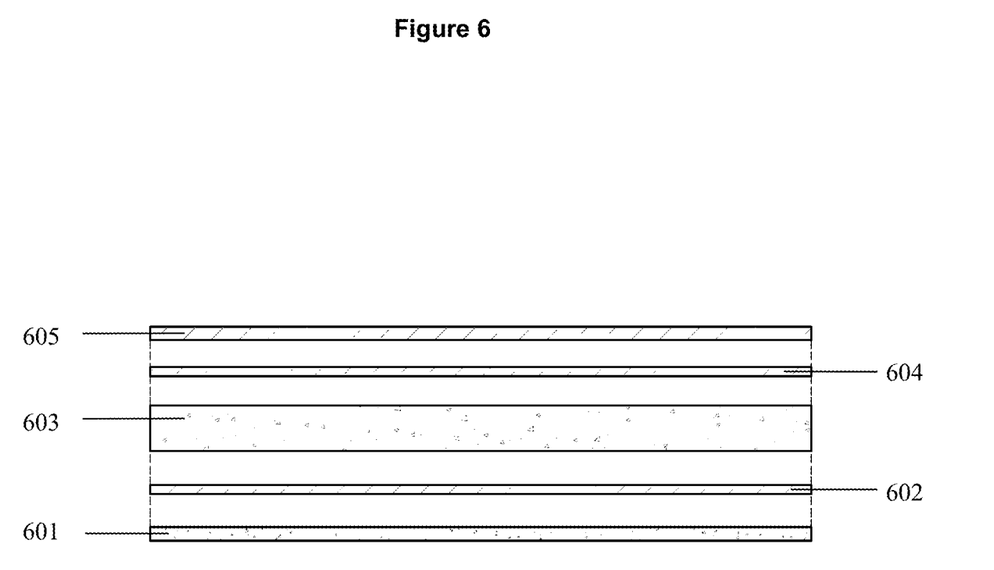
FIG. 6 Shows a cross section through a contiguous portion of a preferred embodiment of the present invention.

Labels placed in the "sense" orientation (that is, not reversed) exemplified by 503, are placed to allow identification of the chambers immediately below the label, while the epicutaneous test plaster is on a patient. Further optional labeling is contemplated by the present invention, by way of non-limiting example chevrons exemplified by 504; which provides an easy means to determine the orientation of the epicutaneous test plaster while on a patient. By way of additional example, markings exemplified by 505 and 506 may be used as a guide for the cutting of the epicutaneous test plaster into individual sections prior to attachment onto a patient; as the epicutaneous test plaster of the present invention is contemplated for use on a patient as an integral patch containing up to 40 chambers (see for example FIG. 9) or as a smaller number of contiguous chambers placed at disparate locations on a patient (see for example FIG. 8). Alternatively perforation of the support and flexible carrier lattice parallel to, or in place of, lines 505 and 506 (not shown) or in directions perpendicular to those markings (not shown), are contemplated by the present invention, the perforations assisting in the easy separation of the epicutaneous test plaster of the present invention into smaller sections. Alternatively the perforations may remain in place following the application of the epicutaneous test plaster to the patient, providing FIG. 6 shows an exploded cross-section of a contiguous portion of the epicutaneous test plaster of the present invention. Support lattice 601, which itself is comprised of a bottom layer that is impermeable to fluid (not shown) on the side of support lattice 601 opposing the flexible carrier lattice 603. Flexible carrier lattice 603 is adhered to support lattice 601 via an adhesive layer 602 interposed between the layers. Removable cover layer 605 is adhered to flexible carrier lattice 603 by way of adhesive layer 604.

Adhesion of the support lattice to the flexible carrier lattice may be undertaken by means generally known in the art, but in a preferred embodiment an adhesive is applied in layer 602, the adhesive selected to have an adhesion strength greater than that between the flexible carrier lattice 603 and removable cover layer 605, and the adhesion strength between flexible carrier lattice 603 and human skin (not shown) when the epicutaneous test plaster is placed on a patient. In a preferred embodiment adhesive layer 602 and 604 are medical grade adhesives, for example methacrylate based adhesives as known in the art. The adhesive used for layer 602 and 604 may be the same, the differential in the adhesion strength between support lattice 601 and flexible carrier lattice 603, and adhesion strength between flexible carrier lattice 603 and removable cover layer 605 arising not from the adhesive used, but from the composition of the removable cover layer.

The composition of flexible carrier lattice 603 is chosen to provide a balance between torsional flexibility of the epicutaneous test plaster on a patient, which is further improved by the holes formed between the support lattice and the flexible carrier lattice; with rigidity useful in the packaging, transport, and addition of haptens to the test chambers formed within the epicutaneous test plaster. Polyethylene foam of between 0.4 mm and 0.6 mm, more preferably 0.5 mm has been found to provide the necessary characteristics, and in a preferred embodiment the flexible carrier lattice is formed by double-sided self-adhesive foam sold by Scapa group Plc, United Kingdom under catalogue number 9742 as "double-sided adhesive tape" of 0.5 mm thickness and 130 mm width.

Figure 7:
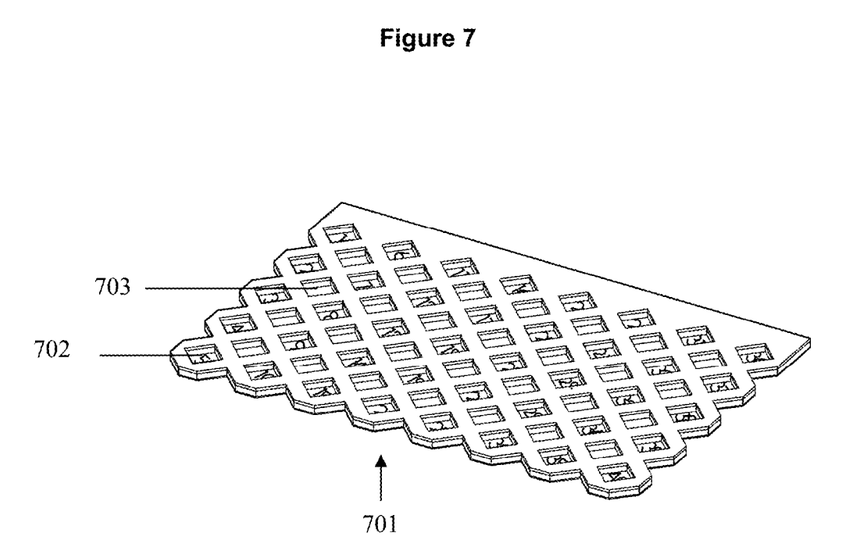
FIG. 7 Shows a preferred embodiment of the present invention with the markings on the support lattice visible in the wells formed by the interface of the support lattice on the carrier lattice.

The removable cover layer of the present invention may be contiguous, covering the chambers formed by the support lattice and flexible carrier lattice, or it may itself be a lattice, with holes superimposed over the holes formed by the support lattice or the flexible carrier lattice. FIG. 7 shows an example of the epicutaneous test plaster of the present invention, with the removable cover layer being a lattice with holes superimposed over the flexible carrier lattice, and optional labelling of the bottom of the support lattice as generally shown in FIG. 5. Epicutaneous test plaster 701 has a series of chambers, 702, with labels read in the "sense" orientation, assisting the user in addition of haptens to chambers 702. Holes 703 pass completely through the epicutaneous test plaster, improving flexibility.

Figure 8:
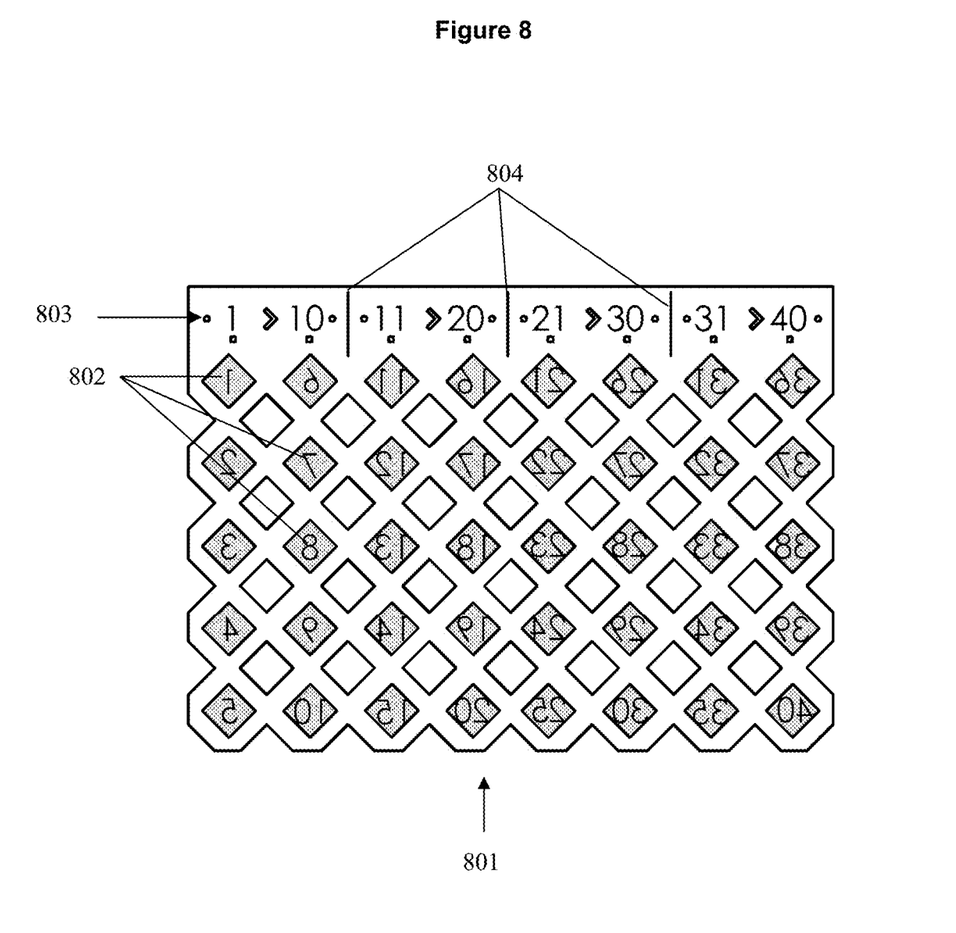
FIG. 8 Shows an exemplary numbering and marking scheme of a preferred embodiment of the present invention.

FIG. 8 provides another perspective of epicutaneous test plaster 801, on the face of the support lattice that portion impermeable to liquid, with chambers 802 formed by the material of the support lattice, and exemplifying the reverse markings useful for loading of the haptens in chambers. Markings 803 are particularly useful for reading the results of the interaction between the haptens placed within the test chambers and the skin of the patient after a period of contact; where portion of the epicutaneous test plaster below markings 803 may be removed and excised (using scissors cutting a horizontal path across the epicutaneous test plaster below, and parallel to, the axis of markings 804) from the patient; while keeping that portion of the epicutaneous test plaster containing markings 803 attached to the patient. In a preferred embodiment, the test chambers 802 ((802)) have a width and length of approximately 8.3 mm, with a depth provided by the flexible carrier lattice of 0.5 mm; resulting in a test chamber volume of approximately 35 microlitres. It is contemplated that the present invention encompasses alternative width and lengths of chamber dimensions, and therefore chamber cross-sectional size and overall volume; and that the chamber dimensions may be different than holes 405 passing through the epicutaneous test plaster.

FIG. 9 Shows patient 901 with epicutaneous test plasters of the present invention, excised to form smaller test plasters with 10 (902) and 15 (903) chambers, placed medially on a patient. FIG. 10 shows placement on patient 1001 of an epicutaneous test plaster of the present invention comprising 32 chambers, 1002.

Figure 11:
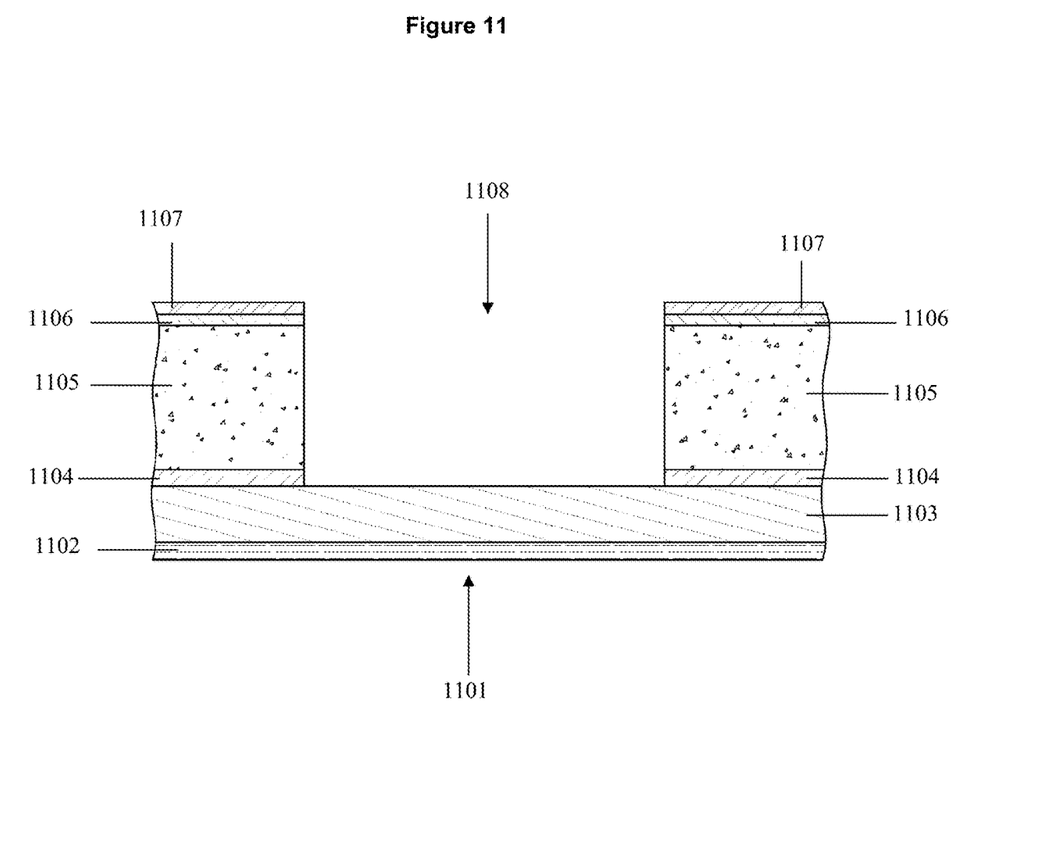
FIG. 11 Shows a cross section of a well of the test plaster of the present invention, formed by the interaction of the support lattice, the flexible carrier lattice, and a removable cover layer.

FIG. 11 shows a cross section through a test chamber of one embodiment of a epicutaneous test plaster of the present invention, 1101. The support lattice is comprised of a layer impermeable to fluid, 1102, and a layer of absorbent material for trapping and containing a hapten, 1103, layer 1103 contemplated as being optional. The flexible carrier lattice is comprised of layers of adhesive, 1104 and 1106, with a polyethylene foam core 1105 between. Removable adhesive layer 1107 protects adhesive layer 1106 until the epicutaneous test plaster is ready to be placed on a patient. Test chamber 1108 is formed by the surrounding flexible carrier lattice and adhesive layer 1104, 1105 and 1106; and bounded on the bottom by support lattice 1102 and optionally layer 1103 should optional absorbent material form part of the support lattice. Optionally, removable carrier layer 1107 may be contiguous, covering test chamber 1108 and protecting it from the elements; though this may require removal of the removable carrier layer 1107 prior to loading of a hapten into test chamber 1108.

While particular embodiments of the present invention have been described in the foregoing, it is to be understood that other embodiments are possible within the scope of the invention and are intended to be included herein. It will be clear to any person skilled in the art that modifications of and adjustments to this invention, not shown, are possible without departing from the spirit of the invention as demonstrated through the exemplary embodiments. The invention is therefore to be considered limited solely by the scope of the appended claims.

What is claimed is:

1. An epicutaneous test plaster comprising
   A support lattice of absorbent paper adhered with a moisture barrier layer containing a first multiplicity of holes,
   A flexible carrier lattice containing a second multiplicity of holes, said flexible carrier lattice including an adhesive layer for removable adhesion of the epicutaneous plaster to a skin portion;
   a removable cover layer extending over all the adhesive layer of said flexible carrier lattice, and
   a plurality of test chambers distributed over the support lattice of absorbent paper adhered with a moisture barrier layer;
   wherein the second multiplicity of holes on the flexible carrier lattice is greater than the first multiplicity of holes on the support lattice of absorbent paper adhered with a moisture barrier;
   wherein said flexible carrier lattice is adhered to the support lattice on the side opposite to the moisture barrier layer;
   wherein the plurality of test chambers are formed by way of a first subset of the second multiplicity of holes in the flexible carrier lattice, wherein each hole of the first subset of the second multiplicity of holes describes a frame around a contiguous portion of the support lattice;
   wherein a second subset of the second multiplicity of holes in the flexible carrier lattice align with the first multiplicity of holes on the support lattice; and
   wherein the removable cover layer is removably secured by way of the adhesive layer of the flexible carrier lattice.

2. The epicutaneous test plaster of claim 1 wherein the flexible carrier lattice is comprised of polyethylene foam and the adhesive layer is comprised of a medical grade adhesive.

3. The epicutaneous test plaster of claim 2 wherein the polyethylene foam has a thickness of between 0.4 mm and 0.6 mm.

4. The epicutaneous test plaster of claim 1 wherein said removable cover layer is a lattice with a third multiplicity of holes.

5. The epicutaneous test plaster of claim 4 wherein said third multiplicity of holes align with the second multiplicity of holes in the flexible carrier lattice.

6. The epicutaneous test plaster of claim 1 wherein at least one unique chamber identifier is printed on the moisture barrier layer proximate to a test chamber.

7. An epicutaneous test plaster comprising
   A support lattice comprising a moisture barrier layer containing a first multiplicity of holes,
   A flexible carrier lattice containing a second multiplicity of holes, said flexible carrier lattice including an adhesive layer for removable adhesion of the epicutaneous plaster to a skin portion;
   a removable cover layer extending over all the adhesive layer of said flexible carrier lattice, and
   a plurality of test chambers distributed over the support lattice;
   wherein the second multiplicity of holes on the flexible carrier lattice is greater than the first multiplicity of holes on the support lattice;
   wherein said flexible carrier lattice is adhered to the support lattice;
   wherein the plurality of test chambers are formed by way of a first subset of the second multiplicity of holes in the flexible carrier lattice, wherein each hole of the first subset of the second multiplicity of holes describes a frame around a contiguous portion of the support lattice;
   wherein a second subset of the second multiplicity of holes in the flexible carrier lattice align with the first multiplicity of holes on the support lattice; and
   wherein the removable cover layer is removably secured by way of the adhesive layer of the flexible carrier lattice.

8. The epicutaneous test plaster of claim 7 wherein the flexible carrier lattice is comprised of polyethylene foam and the adhesive layer is comprised of a medical grade adhesive.

9. The epicutaneous test plaster of claim 8 wherein the polyethylene foam has a thickness of between 0.4 mm and 0.6 mm.

10. The epicutaneous test plaster of claim 7 wherein said removable cover layer is a lattice with a third multiplicity of holes.

11. The epicutaneous test plaster of claim 10 wherein said third multiplicity of holes align with the second multiplicity of holes in the flexible carrier lattice.

12. The epicutaneous test plaster of claim 7 wherein at least one unique chamber identifier is printed on the moisture barrier layer proximate to a test chamber.

\* \* \* \* \*